United States Patent
Ameys (12)

(10) Patent No.: US 6,218,433 B1
(45) Date of Patent: Apr. 17, 2001

(54) USE OF PHARMACEUTICAL COMPOSITION IN THE TREATMENT OF TRAUMATIC ARTHRITIS IN HORSES

(75) Inventor: Jean-Paul Ameys, Brussels (BE)

(73) Assignee: Continental Pharma Incorporated, Louvain-la-Neuve (BE)

( * ) Notice: Subject to any disclaimer, the term of this patent is extended or adjusted under 35 U.S.C. 154(b) by 0 days.

(21) Appl. No.: 09/446,348

(22) PCT Filed: May 20, 1998

(86) PCT No.: PCT/BE98/00074

§ 371 Date: Mar. 20, 2000

§ 102(e) Date: Mar. 20, 2000

(87) PCT Pub. No.: WO98/57623

PCT Pub. Date: Dec. 23, 1998

(30) Foreign Application Priority Data

Jun. 17, 1997 (BE) ................................................ 97870088

(51) Int. Cl.$^7$ .................................................. A61K 31/19
(52) U.S. Cl. ............................................................ 514/575
(58) Field of Search ............................................... 514/575

(56) References Cited

U.S. PATENT DOCUMENTS

| | | | |
|---|---|---|---|
| 4,534,911 | * 8/1985 | Franz et al. ........................... | 514/575 |
| 6,096,728 | * 8/2000 | Collins et al. ........................ | 514/62 |

FOREIGN PATENT DOCUMENTS

| | | | |
|---|---|---|---|
| 1250519 | * 10/1971 | (GB) ................................... | 514/575 |
| 25102/69 | 5/1969 | (US) . | |
| PCT/US96/ 08314 | 5/1996 | (US) . | |
| 96 38418 | * 12/1996 | (WO) .................................. | 514/575 |

OTHER PUBLICATIONS

Lees et al(I), Ann. Rech Vet., vol. 21,pp. 73s–78s, 1990.*
Landoni et al, Equine Vet. J., vol. 28, No. 6, pp. 468–465, 1996.*
Owens et al, Am. J. Vet. Res., vol. 57, No. 6, pp. 866–874, Jun. 1996.*
Denoix et al, Recueil. De Medecine Vet., vol. 168, No. 8–9, pp. 679–698, 1992.*
Lees et al(II), Equine Vet. J., vol. 17, No. 2, pp. 83–96, 1985.*
Suominen et al, Am. J. Vet. Res., vol. 60(12), pp. 1467–1473 (abstract), Dec. 1999.*
Mielants et al, Clin. Rheumatol., vol. 6(1), pp. 55–60 (abstract), Mar. 1987.*
P. Lees et al., Pharmacokinetics and dosage regimens of anti–inflammatory drugs, *Ann Rech Vét*, vol. 21, Suppl. 1, 1990, pp. 73s–78s.
M. F. Landoni et al., Effects of flunixin, tolfenamic acid, R(–) and S(+) ketoprofen on the response of equine synoviocytes to lipopolysaccharide stimulation, *Equine Veterinary Journal*, vol. 28, No 6, 1996, pp. 468–475.
Jane G. Owens et al., Effects of pretreatment with ketoprofen and phenylbutazone on experimentally induced synovitis in horses, *AJVR*, vol. 57, No. 6, Jun. 1996, pp. 866–874.
J. M. Denoix et al., Utilisation des anti–inflammatoires en pathologie articulaire chez le cheval, *Recueil de Médecine Vétérinaire Spécial Anti–inflammatoires*, Sep. 1992, pp. 679–698.
P. Lees et al., Clinical pharmacology and therapeutic uses of non–steroidal anti–inflammatory drugs in the horse, *Equine Veterinary Journal*, vol. 17, No. 2, 1985, pp. 83–96.

* cited by examiner

*Primary Examiner*—James H. Reamer
(74) *Attorney, Agent, or Firm*—Knobbe, Martens, Olson & Bear LLP

(57) ABSTRACT

The present invention is related to the use of a pharmaceutical composition comprising a suitable pharmaceutical carrier and an effective amount of an active compound selected from the group consisting of phenylacetydroxamic acid, phenoxyacetydroxamic acid, arylacetydroxamic acid and/or their corresponding amides, for the preparation of a medicament in the prevention and/or the treatment of equine arthritis.

5 Claims, No Drawings

USE OF PHARMACEUTICAL COMPOSITION IN THE TREATMENT OF TRAUMATIC ARTHRITIS IN HORSES

This application is the U.S. National Phase under 35 U.S.C. §371 of International Application No. PCT/BE98/00074, filed May 20, 1993, which claims priority of European application No. EP 97870088.8, filed on Jun. 17, 1997.

FIELD OF THE INVENTION

The present invention is related to a new use of a pharmaceutical composition comprising an effective amount of phenylacetydroxamic acid, phenoxyacetydroxamic acid, arylacetydroxamic acid, possibly substituted, and/or their corresponding amides.

TECHNOLOGICAL BACKGROUND

It is generally accepted that lameness due to traumatic joint disease in its various forms is a common clinical problem in horses, and one of the most important sources of financial loses in the equine industry (1–9).

Traumatic arthritis can develop after single or repetitive episodes of trauma, but continued repeated trauma to the joint is held as the most important etiologic factor in traumatic arthritis. The mechanical trauma in the form of stretching, impingement and concussion of articular tissues may perturb cellular membranes, resulting in release of inflammatory mediators inciting joint inflammation. In many cases, extended periods of rest are required for the complete resolution of the joint inflammation. Simple resting of the affected horses is therefore seldom an acceptable therapeutic alternative in working horses, considering the limitations of economics, season and competition schedules (6, 10).

On the other hand, if left without proper treatment and the inciting physical activity is continued, the condition of primary acute synovitis-capsulitis often results in devastating chronic changes of the synovial membrane and fibrous joint capsule associated with articular cartilage degeneration. These changes are known to result from prolonged production of the inflammatory mediators and the subsequent production of enzymes capable of degrading the articular cartilage matrix (4, 8, 9).

For these reasons, safe and effective anti-arthritic medications, to be used concurrently with appropriate rehabilitation exercise programs, are necessary in equine medicine.

Classic treatment options for the aseptic arthritis have consisted of systemic administration of non-steroidal anti-inflammatory drugs (NSAIDs) (8, 10, 11) and intra-articular administration of corticosteroids. Various systemic NSAIDs have been proven effective in reducing discomfort and other clinical signs of inflammation associated with traumatic arthritis (12).

However, it is well known that they are of limited value in modifying the course of the disease when the administration is ceased and therefore recurrence of the clinical signs is common after resuming the intended physical activity. Further, NSAID toxicity, especially in high dose or long term use, is of concern in equine species (12).

Intra-articular injection of corticosteroids was first reported in the horse in 1955 (13). Since then it has become certainly the most widely used intra-articular therapy for equine joint inflammation. According to one report 77% of the equine practitioners responding to a questionnaire administered corticosteroids intra-articularly on a regular basis (11). The recognised extensive use of intra-articular corticosteroids, not only in equine medicine, but in human medicine, has stimulated intense research in this field.

Corticosteroids are very important anti-inflammatory agents, suppressing the formation of several mediators of inflammation and articular cartilage degradative enzymes and, as such, effectively reducing the inflammation and pain associated with traumatic joint disease in horses (10). Although there seems to be good rationale for intra-articular corticosteroid therapy in the horse, the safety of this practice, with respect to the articular cartilage metabolism, has been questioned. Recent experimental research has clearly indicated that intra-articularly administered corticosteroids exert several detrimental effects on articular cartilage in equine species (7, 14–23).

Other agents widely used for the local treatment of aseptic arthritis in horses are sodium hyaluronate and polysulphated glycosaminoglycans (PSGAGs). Both of these agents have been found effective (24) and fulfill many of the criteria for an ideal intra-articular drug, but some problems have also been encountered when using these agents. Limited anti-inflammatory action and high cost are the main drawbacks of the hyaluronate preparations (25) whereas PSGAG has been shown to potentiate the development of iatrogenic septic arthritis (26). Severe aseptic adverse reactions to PSGAG have been reported (27, 28). Multiple injections which are in many cases needed to achieve desired therapeutic results with PSGAG not only increase the risks, but also increase the cost and inconvenience of the treatment.

For the given reasons, it is obviously of interest to search for better alternatives for the local therapy of traumatic arthritis in horses.

Other various active compounds such as phenylacetydroxamic acid, phenoxyacetydroxamic acid, arylacetydroxamic acid and/or their corresponding amides, especially the p-butoxyphenylacetydroxamic acid (called Bufexamac, a non-steroidal anti-inflammatory drug, available as a suspension for intra-articular injection) have been used with success for several years, especially in human rheumatology and sports medicine and the clinical efficacy and good tolerance of these drugs has been, reported (29–36). Some early experimental work also suggests that Bufexamac would have an anabolic effect of articular cartilage metabolism by stimulating the synthesis of glycosaminoglycans. This effect has been shown both in in vivo and in vitro experiments using the rate of radiolabelled sulphur incorporation into the cartilage as a measure for the glycosaminoglycan synthesis (37, 38). These active compounds were described in the patents U.S. Pat. No. 3,479,396, BE-611223, BE-661226, BE-648292, LU-84530, and in the European patent application EP-0116182. However, the use of these active compounds has not been previously reported in equine medicine.

The document WO96/38418-A describes anti-inflammatory pharmaceutical agents useful for treating disorders mediated by cyclooxygenase-2 or 5-lipoxygenase like inflammation and allergic conditions such as asthma; said agents are heterocyclo substituted hydroxamic acid derivatives wherein the core structure is sulfonylphenyl. Besides being useful for human treatment, i.e. treatment of arthritis, these compounds are useful for treatment of mammals, including horses.

The document GB-1250519-A describes cyclodecapentaene derivatives which are anti-inflammatory agents, analgesic agents and anti-pyretic agents, which are useful for the treatment of inflammatory conditions and pain associated therewith such as arthritis. They can be administered and used in the same way as phenylbutazone, orally to animals such as horses.

AIMS OF THE INVENTION

The present invention aims to provide a new method for the prevention and/or the treatment of equine arthritis, especially horse arthritis, which does not present the drawbacks of the state of the art.

A main aim of the invention is to provide a method having an extended anti-inflammatory action, which allows the use on low doses of effective amounts of the therapeutical agent and/or which presents reduced side effects.

DESCRIPTION OF THE INVENTION

The present invention is related to the use of a pharmaceutical composition comprising a suitable pharmaceutical carrier and an effective amount of an active compound selected from the group consisting of phenylacetydroxamic acid, preferably the Bufexamac (p-butoxyphenylacetydroxamic acid), phenoxyacetydroxamic acid, arylacetydroxamic acid, possibly substituted, and/or their corresponding amides, for the preparation of a medicament in the prevention and/or the treatment of equine arthritis.

The present invention is also related to a prevention and/or treatment method of equine arthritis, comprising the step of administering to a horse a pharmaceutical composition comprising a suitable pharmaceutical carrier and an effective amount of an active compound selected from the group consisting of phenylacet-ydroxamic acid, preferably the Bufexamac (p-butoxyphenylacetydroxamic acid), phenoxyacetydroxamic acid, arylacetydroxamic acid, possibly substituted, and/or their corresponding amides.

The Inventors have discovered unexpectedly that an effective amount of the above-identified active compounds, which has never been previously reported in equine medicine, can be advantageously used in the prevention and/or the treatment of equine arthritis.

As used herein, "an effective amount of an active compound" means an amount sufficient to at least ameliorate or prevent the symptoms of equine arthritis. This effective amount may vary depending on such factors as the state of the conditions being treated, the overall health of the animal, the method of administration, the severity of the side effects and the like.

However, the Inventors have discovered unexpectedly that the doses of the active compounds used in the method according to the invention comprise between 20 and 60 mg/500 kg body weight (bw) in horses.

The doses per bw used for the treatment of equine arthritis, are unexpected in view of the experiments already made upon humans, wherein the usual doses are 20 mg/70 kg body weight in humans.

In addition, contrary to the products of the state of the art (especially the NSAIDs), the active compounds according to the invention do not present any systemic side effect, even in case of long term or high dose administration.

Even with long term high dose administration, no deleterious effect on equine cartilage was observed with the active compounds according to the invention.

These results are particularly unexpected for the active compounds according to the invention, which are considered as xenobiotic drugs.

In addition, the pharmaceutical composition according to the invention may comprise suitable pharmaceutical carriers or adjuvants which may vary according to the mode of administration.

Preferably, said suitable pharmaceutical carriers or adjuvants are common carriers or adjuvants well known by the man skilled in the art and used to increase the therapeutical effects and/or the decrease of the side-effects of p-butoxyphenylacetydroxamic acid.

The pharmaceutical composition according to the invention is prepared according to the methods generally applied by pharmacists and may include solid or liquid, non-toxic and pharmaceutically acceptable vehicles or carriers.

The percentage of the active product/suitable pharmaceutical carriers can vary within a very large range, only limited by the tolerance and the level of the habit-forming effect of the product to the animal. The limits are particularly determined by the frequency of administration to the animal.

Preferably, said pharmaceutical composition is an intra-articularly injectable composition.

According to a preferred embodiment of the present invention, said pharmaceutical composition further comprises an active compound selected from the group consisting of other non-steroidal anti-inflammatory drugs (NSAIDs), corticosteroids, glycosaminoglycans such as sodium hyaluronate and polysulphated glycosaminoglycan (PSGAG) and/or a mixture thereof.

Said preferred pharmaceutical composition may be used for a synergic effect obtained by the various therapeutic compounds against equine arthritis.

The present invention will be described in detail in the following examples, which are various illustrations of the method according to the invention without limiting its scope.

EXAMPLES

1. Effect of Intra-articularly Administered Bufexaniac Suspension on Experimentally Induced Aseptic Arthritis in Horses: Dose-titration Study This experiment aims to assess the clinical efficacy of intra-articularly administered Bufexamac suspension in the treatment of amphotericin B-induced aseptic arthritis, define the optimal intra-articular dose of a Bufexamac suspension, assess the effects of intra-articular Bufexamac on various synovial fluid parameters as well as on histologic features of the synovial membrane and histochemical features of the articular cartilage in horses with amphotericin B-induced aseptic arthritis.

The efficacy and dose response of intraarticularly injected Bufexamac suspension were evaluated in this randomised double blind trial, using 24 healthy horses in which aseptic arthritis was created by intra-articular injection of amphoterycin B ® to induce synovitis-capsulitis in one intercarpal joint of each horse. The horses were randomised with three treatment groups and one control group. The effects of experimental treatment with Bufexamac suspension were evaluated by comparing various clinical and synovial fluid parameters between the groups. Radiographic, gross pathologic, histopathologic and histochemical findings were also used in the evaluation of the treatment effects.

2. Effect of Intra-articularly Administered Bufexamac Suspension on Synovia in Horses: Pilot Safety Study This experiment aims to make a preliminary assessment of the local and systemic effects of a single 5× intra-articular dose of Bufexamac suspension.

The high doses used in this experiment are chosen in order to demonstrate the good tolerance of the active compounds according to the invention by horses.

The effects of intra-articularly injected Bufexamac suspension on various synovial fluid parameters was evaluated in this self-controlled trial by using 4 healthy horses, in which a large single dose (5×) of the drug to be tested was injected into one metacarpophalangeal joint of each horse. The contralateral joint served as a control. The evolution of the treatment effects was performed by comparing the synovial fluid findings between the test and the control joints. In addition to the routine synovial fluid analysis, special attention was paid to the determination of the proteoglycans in the synovial fluid. The local and systemic tolerance of the drug to be tested was also evaluated by means of daily clinical examinations and by serial determinations of various haematologic variables.

3. Local and Systemic Tolerance of Intra-articularly Administered Bufexamac Suspension in Horses: Multiple-dose Safety Study This experiment aims to:
assess the local and systemic tolerance of intra-articular Bufexamac suspension in healthy horses,
define the margin of safety of intra-articular Bufexamac suspension in horses.

Both local and systemic tolerance of intra-articularly injected Bufexamac suspension was evaluated in this well controlled and randomised blinded trial using 20 healthy horses. The horses were randomised into three treatment groups and one control group, five horses in each. Each horse was treated intra-articularly either with sterile saline as a negative control or with one of the three selected doses (1×-3×-5× of the recommended dose) of Bufexamac suspension into one intercarpal joint for a total of six weekly injections (i.e. 1×-2×-3× the duration of a normal treatment). The effects of the experimental treatment with Bufexamac suspension were evaluated by comparing various clinical, haematologic, serum chemistry and synovial fluid parameters between the groups. Radiographic, arthroscopic, gross pathologic, histopathologic and histochemical findings were also used in the evaluation of the treatment effects.

It was demonstrated that bufexine, a sterile 2% injectable suspension of Bufexamac, was perfectly safe when administered intra-articularly in horses. This conclusion was based on the fact that no significant untoward effects, whether systemic or local, could be observed in animals treated with intra-articular bufexine using dosages up to 5× the recommended dose repeated at weekly intervals for a total of 6 treatments.

Mild to moderate heat and/or effusion of the treated joints resolving completely within 24–72 hours were seen occasionally as only side-effects. These signs were not associated with pain in any of the cases affected. Since these signs were seen in comparable numbers in placebo treated control animals too, a technique related cause remains a possibility.

These conclusions were further confirmed by the results of the gross pathologic examinations, histopathologic examinations of the main internal organs and articular target tissues as well as histochemical examinations of the articular target tissues.

REFERENCES

1. Jeffcott, L. B. et al., An assessment of wastage in Thoroughbred racing from conception to 4 years of age, Equine Vet. J., 14, pp. 185–198 (1982)
2. Kobluck, C. N. et al., Comparison of the exercise level and problem rate of 95 Thoroughbred horses: A cohort study, in Proceedings of the $36^{th}$ Ann. Meet. AAEP, pp. 471–475 (1990)
3. Rossdale P. D. et al., Epidemiological study of wastage among racehorses from 1982 to 1983, Vet. Rec., 116, pp. 66–69 (1985)
4. Todhunter R. J. et al., Synovial Joint Anatomy, Biology and Pathology, in Equine Surgery. Ed. J. A. Auer W. B. Saunders Company, Philadelphia, p. 8444 (1992)
5. McIlwraith C. W., Intra-articular medication in the treatment of osteoarthritis. Communication at Fourth Annual SCentific Meeting of the ECVS, Constance, Germany, Jun. 30–Jul. 2 (1995)
6. Palmer, J. L. et al., Experimentally induced synovitis as a model for acute synovitis in the horse, Equine Vet. J., 26, pp. 492–495 (1994)
7. Palmer, J. L. et al., Joint structure, biochemistry and biochemical disequilibrium in synovitis and equine joint disease, Equine Vet. J., 26, pp. 263–277 (1994)
8. McIlwraith, C. W., Disease of joints, tendons, ligaments, and related structures. In: Adam's Lameness in Horses. Ed. TS Stashak Lea and Febiger, Philadelphia, pp. 360–395 (1987)
9. Todhunter, R. J. et al., Pathophysiology of synovitis Clinical signs and examination in horses. Comp. Cont. Educ. Pract. Vet., 12, pp. 980–992 (1990)
10. Richardson, D. W., Medical Treatment of Degenerative Joint Disease. In Equine Medicine and Surgery. Ed. Colahan PT et al. American Veterinary Publications, California, pp. 1259–1260 (1991)
11. Todhunter, R. J. et al., Therapeutic Principles for Joint Disease and Repair of Articular Tissues. In Equine Surgery. Ed. J. A. Auer W. B. Saunders Company, Philadelphia, pp. 885–890 (1992)
12. Lees, P. et al., Clinical pharmacology and therapeutics uses of non-steroidal anti-inflammatory drugs in the horse. Equine Vet. J., 17, pp. 83–96 (1985)
13. Wheat, J. D., The use of hydrocortisone in the treatment of joint and tendon disorders in large animals, J. am. Vet. Med. Assoc., 127, pp. 64–67 (1955)
14. Fubini, S. L. et al., Effects of intramuscularly administered polysulfated glycosaminoglycan on articular cartilage from equine joints injected with methylprednisolone acetate. Am. J. Vet. Res., 54, pp. 1359–1385 (1993)
15. McKay A. G. et al., Observations of the intra-articular use of corticosteroids in the racing Thoroughbred. J. Am. Vet. Med. Assoc., 168, pp. 1039–1041 (1976)
16. O'Connor J. T., The untoward effects of the corticosteroids in equine practice. J. Am. Vet. Med. Assoc., 153, pp. 1614–1617 (1968)
17. Meagher, D. AM, The effects of intra-articular corticosteroids and continued training on carpal chip fractures of horses. In Proceedings of the Ann. Meet. AAEP, 16, pp. 405–412 (1979)
18. Owen, R. et al., Intra-articular corticosteroid and exercise induced arthropathy in a horse. J. Am. Vet Med. Assoc., 194, pp. 302–308 (1984)
19. Chunekamrai, S. te al., Changes in articular cartilage after intra-articular injections of methylprednisolone acetate in horses. Am. J. Vet. Res., 50, pp. 1733–1741 (1989)
20. Trotter, G. W. et al., Effects of methylprednisolone acetate on equine articular cartilage. Am. J. Vet. Res., 52, pp. 83–87 (1991)
21. Shoemaker, S. R. et al., Effects of intra-articular administration of methylprednisolone acetate on equine articular cartilage and on healing of experimentally induced osteochondral defects in horses. Am. J. Vet. Res., 53, pp. 1446–1453 (1992)

22. Roneus, B. et al., Effects of intra-articular corticosteroids and sodium hyaluronate injections on synovial fluid production and synovial fluid content of sodium hyaluronate and proteoglycans in normal equine joints. J. Vet. Med. A, 40, pp. 10–16 (1993)
23. Saari, H. T. et al., Methylprednisolone acetate induced release of cartilage proteoglycans Analysis with high-performance liquid chromatography HPLC. Ann. Rheum. Dis., 51, pp. 214–219 (1992)
24. Gaustad, G. et al., Comparison of polysulphated glycosaminoclycan and sodium hyaluronate with placebo in treatment of traumatic arthritis in horses. Equine Vet. J., 27, pp. 356–362 (1995)
25. McIlwraith, C. W. et al., review of pathogenesis and treatment of degenerative joint disease. In Equine Orthopaedic Injury and Repair. Equine Vet. J. (Suppl) 6, pp. 3–11 (1988)
26. Richardson, D. W., Medical Treatlment of Degenerative Joint Disease. In Equine Medicine and Surgery. Ed. Colahan PT et al. American Veterinary Publications, California, p. 1261 (1991)
27. Gustafson, S. B. et al., Comparison of the effect of polysulfated glycosaminoglycan, corticosteroids and sodium hyaluronate in the potentiation of a subinfective dose of staphylococcus aureus in the midcarpal joint of horses. Am. J. Vet. Res., 50, p. 2014 (1989)
28. MAY, S. A., Anti-inflammatory Agents. In Current Therapy in Equine Medicine. Ed. Robinson NE W. B. Saunders Company, Philadelphia, p. 17 (1992)
29. Mardjuadi, A. et al., Double-blind trial comparing Bufexamac infiltrations with triamcinolone acetonide infiltrations in patients with peri-arthritis of the shoulder. Current Medical Research and Opinion, 5, No. 5 (1978)
30. Wauters, M., Clinical stuides with Bufexamac, a non-steroid anti-inflammatory drug, by intra- or peri-articular administration. Current Therapeutic research, 23, No. 6 (1978)
31. Dieux, F. et al., Etude comparative, en double insu, du Bufexamac et de l'acétonide de triamcinolone en injection locale dans le rhumatisme articulaire et les arthroses. Acta Rheumatologica, 3, Fasc. 4 (1979)
32. Borms, T. et al., Vergelijkende studie, Bufexamac i.a./triamcinolone i.a. (arthrosis, PSH, tendinitis, . . . ). personal communication
33. Commandre, F. A. et al., Etude controlee en double aveugle comparant le Bufexamac et la bêtaméthasone dans les traumatismes d'origine sportive et l'arthrose. Medecine du Sport, 57, No. 5 (1983)
34. Etienne, J. C., Etude en double insu comparant le Bufexamac et la bêtaméthasone en medecine des sports. Personnal Communication
35. Martens, M. et al., Conservatieve behandeling van sportletsels een dubbel blind studie Bufexamac-triamcinolone. Tijdschr. Voor Geneeskunde, 42, pp. 261–1264 (1986)
36. Van Stalle, F., Bufexine en médecine sportive—Etude coopérative en clair. Personnal Communication
37. Van Cauwenberge, H. et al., Etude expérimentale et clinique d'un nouvel anti-inflammatoire non stéroïdien: acide butoxyphenylacet hydroxamique (Droxaryl). J belg. Med. Phys., 23, pp. 133–148
38. Roba, J., Communication at the XII Congress Rheumatology, Prague, Oct. 8–11 (1968)

What is claimed is:

1. A method for the prevention and/or treatment of equine arthritis, comprising administering a suitable pharmaceutical carrier and an effective amount of an active compound selected from the group consisting of phenylacetydroxamic acid, phenoxyacetydroxamic acid, arylacetydroxamic acid and their corresponding amides, wherein said compound is administered by intra-articular injection.

2. The method of claim 1, wherein the active compound is p-butoxyphenylacetydroxamic acid (Bufexamac).

3. The method of claim 1 wherein the effective amount comprises between about 20 and about 60 mg/500 kg horse body weight.

4. The method of claim 1 wherein the pharmaceutical composition further comprises an active compound chosen from the group consisting of other non-steroidal antinflammatory drugs (NSAIDs), corticosteroids, glycosaminoglycans a mixture thereof.

5. The method of claim 4 wherein the glycosaminoglycans are sodium hyaluronate or polysulphated glycosaminoglycan (PSGAG).

* * * * *